United States Patent
Cheng et al.

(10) Patent No.: US 7,316,710 B1
(45) Date of Patent: Jan. 8, 2008

(54) FLEXIBLE STENT

(75) Inventors: E Tina Cheng, Union City, CA (US); Santosh Prabhu, San Jose, CA (US); Kyle Marie Krueger, San Jose, CA (US); Diem Uyen Ta, San Jose, CA (US); Carla Rosa Pienknagura, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 636 days.

(21) Appl. No.: 10/334,033

(22) Filed: Dec. 30, 2002

(51) Int. Cl.
 *A61F 2/86* (2006.01)
(52) U.S. Cl. ..................................... 623/1.15
(58) Field of Classification Search ............ 623/1.15, 623/1.16, 1.17
 See application file for complete search history.

(56) References Cited

U.S. PATENT DOCUMENTS

| | | |
|---|---|---|
| 2,701,559 A | 2/1955 | Cooper |
| 3,105,492 A | 10/1963 | Jeckel |
| 3,657,744 A | 4/1972 | Ersek |
| 3,868,956 A | 3/1975 | Alfidi et al. |
| 3,993,078 A | 11/1976 | Bergentz et al. |
| 4,130,904 A | 12/1978 | Whalen |
| 4,140,126 A | 2/1979 | Choudhury |
| 4,159,719 A | 7/1979 | Haerr |
| 4,323,071 A | 4/1982 | Simpson |
| 4,387,952 A | 6/1983 | Slusher |
| 4,503,569 A | 3/1985 | Dotter |
| 4,504,354 A | 3/1985 | George et al. |
| 4,512,338 A | 4/1985 | Balko et al. |
| 4,516,972 A | 5/1985 | Samson |
| 4,531,933 A | 7/1985 | Norton et al. |
| 4,553,545 A | 11/1985 | Maass et al. |
| 4,560,374 A | 12/1985 | Hammerslag |
| 4,580,568 A | 4/1986 | Gianturco |
| 4,616,652 A | 10/1986 | Simpson |
| 4,619,246 A | 10/1986 | Molgaard-Nielsen et al. |
| 4,649,922 A | 3/1987 | Wiktor |
| 4,650,466 A | 3/1987 | Luther |

(Continued)

FOREIGN PATENT DOCUMENTS

DE 3640745 A1 6/1987

(Continued)

OTHER PUBLICATIONS

Dotter, Charles T. Transluminally Placed Coilspring Endarterial Tube Grafts, *Investigative Radiology*, pp. 329-332, Sep./Oct. 1969.

(Continued)

*Primary Examiner*—Michael Thaler
(74) *Attorney, Agent, or Firm*—Fulwider Patton LLP

(57) ABSTRACT

The present invention is directed to a flexible expandable stent for implantation in a body lumen, such as a coronary artery. The stent generally includes a series of metallic cylindrical rings longitudinally aligned on a common axis of the stent and interconnected by a series of links which be polymeric or metallic. Varying configurations and patterns of the links and rings provides longitudinal and flexural flexibility to the stent while maintaining sufficient column strength to space the cylindrical rings along the longitudinal axis and providing a low crimp profile, enhanced stent security and radial stiffness.

11 Claims, 8 Drawing Sheets

U.S. PATENT DOCUMENTS

| | | |
|---|---|---|
| 4,655,771 A | 4/1987 | Wallsten |
| 4,665,918 A | 5/1987 | Garza et al. |
| 4,681,110 A | 7/1987 | Wiktor |
| 4,706,671 A | 11/1987 | Weinrib |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,760,849 A | 8/1988 | Kropf |
| 4,762,128 A | 8/1988 | Rosenbluth |
| 4,767,418 A | 8/1988 | Deininger et al. |
| 4,768,507 A | 9/1988 | Fischell et al. |
| 4,776,337 A | 10/1988 | Palmaz |
| 4,795,458 A | 1/1989 | Regan |
| 4,800,882 A | 1/1989 | Gianturco |
| 4,830,003 A | 5/1989 | Wolff et al. |
| 4,848,343 A | 7/1989 | Wallsten et al. |
| 4,856,516 A | 8/1989 | Hillstead |
| 4,870,966 A | 10/1989 | Dellon et al. |
| 4,877,030 A | 10/1989 | Beck et al. |
| 4,878,906 A | 11/1989 | Lindemann et al. |
| 4,886,062 A | 12/1989 | Wiktor |
| 4,887,997 A | 12/1989 | Okada |
| 4,892,539 A | 1/1990 | Koch |
| 4,893,623 A | 1/1990 | Rosenbluth |
| 4,907,336 A | 3/1990 | Gianturco |
| 4,913,141 A | 4/1990 | Hillstead |
| 4,921,479 A | 5/1990 | Grayzel |
| 4,922,905 A | 5/1990 | Strecker |
| 4,923,464 A | 5/1990 | DiPisa, Jr. |
| 4,943,346 A | 7/1990 | Mattelin |
| 4,950,227 A | 8/1990 | Savin et al. |
| 4,963,022 A | 10/1990 | Sommargren |
| 4,969,458 A | 11/1990 | Wiktor |
| 4,969,890 A | 11/1990 | Sugita et al. |
| 4,986,831 A | 1/1991 | King et al. |
| 4,988,356 A | 1/1991 | Crittenden et al. |
| 4,990,155 A | 2/1991 | Wilkoff |
| 4,994,071 A | 2/1991 | MacGregor |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,059,211 A | 10/1991 | Stack et al. |
| 5,061,273 A | 10/1991 | Yock |
| 5,061,275 A | 10/1991 | Wallsten et al. |
| 5,062,829 A | 11/1991 | Pryor et al. |
| 5,064,435 A | 11/1991 | Porter |
| 5,071,407 A | 12/1991 | Termin et al. |
| 5,073,694 A | 12/1991 | Tessier et al. |
| 5,078,720 A | 1/1992 | Burton et al. |
| 5,078,726 A | 1/1992 | Kreamer |
| 5,078,736 A | 1/1992 | Behl |
| 5,084,065 A | 1/1992 | Weldon et al. |
| 5,089,005 A | 2/1992 | Harada |
| 5,089,006 A | 2/1992 | Stiles |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,416 A | 4/1992 | Ryan et al. |
| 5,108,417 A | 4/1992 | Sawyer |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,158,548 A | 10/1992 | Lau et al. |
| 5,161,547 A | 11/1992 | Tower |
| 5,163,951 A | 11/1992 | Pinchuk et al. |
| 5,163,952 A | 11/1992 | Froix |
| 5,163,958 A | 11/1992 | Pinchuk |
| 5,171,262 A | 12/1992 | MacGregor |
| 5,180,368 A | 1/1993 | Garrison |
| 5,183,085 A | 2/1993 | Timmermans |
| 5,192,297 A | 3/1993 | Hull |
| 5,192,307 A | 3/1993 | Wall |
| 5,192,311 A | 3/1993 | King et al. |
| 5,195,984 A | 3/1993 | Schatz |
| 5,197,978 A | 3/1993 | Hess |
| 5,217,482 A | 6/1993 | Keith |
| 5,222,971 A | 6/1993 | Willard et al. |
| 5,226,913 A | 7/1993 | Pinchuk |
| 5,234,456 A | 8/1993 | Silvestrini |
| 5,242,394 A | 9/1993 | Tremulis |
| 5,242,399 A | 9/1993 | Lau et al. |
| 5,242,452 A | 9/1993 | Inoue |
| 5,282,823 A | 2/1994 | Schwartz et al. |
| 5,282,824 A | 2/1994 | Gianturco |
| 5,290,295 A | 3/1994 | Querals et al. |
| 5,290,305 A | 3/1994 | Inoue |
| 5,292,331 A | 3/1994 | Boneau |
| 5,304,200 A | 4/1994 | Spaulding |
| 5,314,444 A | 5/1994 | Gianturco |
| 5,314,472 A | 5/1994 | Fontaine |
| 5,330,500 A | 7/1994 | Song |
| 5,344,426 A | 9/1994 | Lau et al. |
| 5,354,308 A | 10/1994 | Simon et al. |
| 5,356,433 A | 10/1994 | Rowland et al. |
| 5,360,401 A | 11/1994 | Turnland et al. |
| 5,368,566 A | 11/1994 | Crocker |
| 5,372,600 A | 12/1994 | Beyar et al. |
| 5,378,239 A | 1/1995 | Termin et al. |
| 5,383,892 A | 1/1995 | Cardon et al. |
| 5,405,378 A | 4/1995 | Strecker |
| 5,421,955 A | 6/1995 | Lau et al. |
| 5,423,745 A | 6/1995 | Todd et al. |
| 5,423,885 A | 6/1995 | Williams |
| 5,445,646 A | 8/1995 | Euteneuer et al. |
| 5,449,373 A | 9/1995 | Pinchasik et al. |
| 5,456,694 A | 10/1995 | Marin et al. |
| 5,458,615 A | 10/1995 | Klemm et al. |
| 5,476,476 A | 12/1995 | Hillstead |
| 5,484,449 A | 1/1996 | Amundson et al. |
| 5,507,768 A | 4/1996 | Lau et al. |
| 5,514,154 A | 5/1996 | Lau et al. |
| 5,545,132 A | 8/1996 | Fagan et al. |
| 5,571,135 A | 11/1996 | Fraser et al. |
| 5,603,721 A | 2/1997 | Lau et al. |
| 5,626,604 A | 5/1997 | Cottone, Jr. |
| 5,653,690 A | 8/1997 | Booth et al. |
| 5,653,691 A | 8/1997 | Rupp et al. |
| 5,653,727 A | 8/1997 | Wiktor |
| 5,690,644 A | 11/1997 | Yurek et al. |
| 5,716,396 A | 2/1998 | Williams, Jr. |
| 5,720,726 A | 2/1998 | Marcadis et al. |
| 5,733,303 A | 3/1998 | Israel et al. |
| 5,733,325 A | 3/1998 | Robinson et al. |
| 5,735,893 A | 4/1998 | Lau et al. |
| 5,782,855 A | 7/1998 | Lau et al. |
| 5,800,521 A | 9/1998 | Orth |
| 5,810,871 A | 9/1998 | Tuckey et al. |
| 5,817,152 A | 10/1998 | Birdsall et al. |

| | | | |
|---|---|---|---|
| 5,830,217 A | 11/1998 | Ryan | |
| 5,836,965 A | 11/1998 | Jendersee et al. | |
| 5,836,966 A * | 11/1998 | St. Germain | 606/198 |
| 5,893,852 A | 4/1999 | Morales | |
| 5,902,332 A | 5/1999 | Schatz | |
| 5,984,964 A | 11/1999 | Roberts et al. | |
| 5,997,468 A | 12/1999 | Wolff et al. | |
| 6,030,413 A | 2/2000 | Lazarus | |
| 6,066,168 A | 5/2000 | Lau et al. | |
| 6,146,358 A | 11/2000 | Rowe | |
| 6,273,911 B1 * | 8/2001 | Cox et al. | 623/1.15 |
| 6,380,457 B1 | 4/2002 | Yurek et al. | |
| 6,475,236 B1 * | 11/2002 | Roubin et al. | 623/1.15 |
| 6,663,663 B2 * | 12/2003 | Kim et al. | 623/1.15 |
| 6,755,855 B2 | 6/2004 | Yurek et al. | |
| 6,863,685 B2 * | 3/2005 | Davila et al. | 623/1.34 |
| 2002/0095140 A1 * | 7/2002 | Lootz et al. | 606/1 |

FOREIGN PATENT DOCUMENTS

| | | |
|---|---|---|
| DE | 3823060 A1 | 1/1989 |
| EP | 0 062 300 A2 | 10/1982 |
| EP | 0 221 570 A2 | 5/1987 |
| EP | 0 338 816 A2 | 10/1989 |
| EP | 0 361 192 A3 | 4/1990 |
| EP | 0 364 787 A1 | 4/1990 |
| EP | 0 372 789 A3 | 6/1990 |
| EP | 0 380 668 A1 | 8/1990 |
| EP | 0 407 951 A3 | 1/1991 |
| EP | 9 408 245 A1 | 1/1991 |
| EP | 0 421 729 A2 | 4/1991 |
| EP | 0 423 916 A1 | 4/1991 |
| EP | 0 428 479 A1 | 5/1991 |
| EP | 0 517 075 B1 | 12/1992 |
| EP | 0 540 290 A2 | 5/1993 |
| EP | 0 541 443 A1 | 5/1993 |
| EP | 0 807 424 A2 | 11/1997 |
| FR | 2 677 872 | 12/1992 |
| GB | 2 070 490 A | 9/1981 |
| GB | 2 135 585 A | 11/1983 |
| JP | 58-501458 | 9/1983 |
| JP | 62-213762 | 9/1987 |
| JP | 62-231657 | 10/1987 |
| JP | 62-235496 A | 10/1987 |
| JP | 63-214264 | 9/1988 |
| JP | 63-246178 | 10/1988 |
| JP | 64-83685 | 3/1989 |
| JP | 01083685 A | 3/1989 |
| JP | 1-299550 | 12/1989 |
| JP | 2-174859 | 7/1990 |
| JP | 2 255157 | 10/1990 |
| JP | 03009745 A | 1/1991 |
| JP | 03009746 A | 1/1991 |
| JP | 3-57465 | 3/1991 |
| JP | 3-151983 | 6/1991 |
| JP | 4-25755 | 2/1992 |
| WO | WO 89/01798 | 3/1989 |
| WO | WO 89/08433 | 9/1989 |
| WO | WO 91/07139 | 5/1991 |
| WO | WO 92/06734 | 4/1992 |
| WO | WO 92/09246 | 6/1992 |

OTHER PUBLICATIONS

Dotter, Charles T., Transluminal Expandable Nitinol Coil Stent Grafting: Preliminary Report, *Radiology Journal*, pp. 259-260, Apr. 1983.

Cragg et al., Non-Surgical Placement of Arterial Endoprostheses: A New Technique Using Nitinol Wire, *Radiology Journal*, pp. 261-263, Apr. 1983.

Maass, et al., Radiological Follow-Up of Transluminally Inserted Vascular Endoprostheses: An Experimental Study Using Expanding Spirals, *Radiology Journal*, pp. 659-663, 1984.

C.R. Bard, PE Plus Peripheral Balloon Dilation Catheter, *C.R. Bard, Inc.*, Aug. 1985.

Wright, et al., Percutaneous Endovascular Stents: An Experimental Evaluation, *Radiology Journal*, pp. 69-72, 1985.

Palmaz et al., Expandable Intraluminal Graft: A Preliminary Study, *Radiology Journal*, pp. 73-77, 1985.

Duprat et al., Flexible Balloon-Expanded Stent For Small Vessels, *Radiology Journal*, pp. 276-278 (1987).

Yoshioka et al., Self-Expanding Endovascular Graft: An Experimental Study in Dogs, *American Journal of Roentgeriology*, pp. 673-676, vol. 151, Oct. 1988.

Rosch, Jr., M.D. et al., Transjugular Intrahepatic Portacaval Shunt: An Experimental Work, *The American Journal of Surgery*, pp. 588-592, vol. 121, May 1971.

70th Scientific Assembly and Annual Meeting: Scientific Program, *Radiology*, Washington, D.C., Nov. 25-30, 1984, special Edition, vol. 153(P).

Charnsangavej, D., M.D. et al., Endovascular Stent for Use in Aortic Dissection: An In Vitro Experiment, *Radiology*, pp. 323-324, vol. 157, No. 2, Nov. 1985.

72nd Scientific Assembly and Annual Meeting: RSNA Scientific Program, *Radiology*, Chicago: Nov. 30-Dec. 5, 1986, Special Edition, vol. 161(P).

Wallace, Michael J., et al., *Tracheobronchia* Tree: Expandable Metallic Stents Used in Experimental Clinical Applications (Work in Progress), *Radiology*, pp. 309-312, vol. 158, Feb. 1986.

Program: Day 2 (Nov. 18) The Radiological Society of North America, *Radiology*, Chicago: Nov. 30-Dec. 5, 1986, Special Edition, vol. 161(P).

Charnsangavej, Chusilp, M.D., et al., Stenosis of the Vena Cava: Preliminary Assessment of Treatment with Expandable Metallic Stents, *Radiology*, pp. 295-298, vol. 161, Nov. 1986.

Rosch, Josef, M.D., et al., Experimental Intrahepatic Portacaval Anastomosis: Use of Expandable Gianturco Stents, *Radiology*, pp. 481-485, vol. 162, Feb. 1987.

Rosch, Josef, M.D., et al., Gianturco Expandable Stents in Experimental and Clinical Use, paper presented at The Twelfth Annual Course on "Diagnostic Angiography and Interventional Radiology" Mar. 23-26, 1987 (Pittsburg, Pennsylvania).

Finci, Leo, M.D., et al., Percutaneous Transluminal Coronary Angioplasty of a Bifurcation Narrowing Using the Kissing Wire Monorail Balloon Technique, *The American Journal of Cardiology*, pp. 375-376, vol. 60, Aug. 1987.

Lawrence, David D., Jr., M.D., et al., Percutaneous Endovascular Graft: Experimental Evaluation, *Radiology*, pp. 357-360, vol. 163, May 1987.

Rosch, Josef, M.D., et al., Gianturco Expandable Wire Stents in the Treatment of Superior Vena Cava Syndrome Recurring after Maximum—Tolerance Radiation, *Cancer*, pp. 1243-1246, vol. 60, Sep. 1987.

Bonzel, T., et al., The Sliding Rail System (Monorail): Descriptionof a New Technique for Intravascular Instrumentation and Its Application to Coronary Angioplasty, *Kardiologie*, Supplement 6, pp. 119-122, 1987.

Rosch, Josef, M.D., et al., Modified Gianturco Expandable Wire Stents in Experimental and Clinical Use, *Annales de Radiologie*, pp. 100-103, vol. 31, No. 2, 1988.

Yoshioka et al., Development and Clinical Application of Biliary Endoprosthesis Using Expandable Metallic Stents, *Japan Radiological Society*, 1988, vol. 48, No. 9, pp. 1183-1185 (with translaton).

Mirich, et al., Percutaneously Placed Endovascular Grafts for Aoertic Aneurysms: Feasibility Study, *Radiology*, 1989, part 2, pp. 1033-1037.

Furui, Shigeru, M.D., et al., Hepatic Inferior Vena Cava Obstruction: Treatment of Two Types with Gianturco Expandable Metallic Stents, *Radiology*, pp. 665-670, Sep. 1990.

Kaltenbach, M., Prof. Dr., Abstracts, *Zeitschrift fur Kardiologie*, Apr. 3, 1991 (Germany Only).

van der Geissen, Willem J., et al., Coronary Stenting with a New, Radiopaque Balloon-Expandable Endoprosthesis in Pigs, *Circulation*, vol. 83, No. 5, pp. 93-149, May 1991.

Strupp, G., et al., Clinical and Angiographic Short and Medium Term Results after Coronary Stenting, *Zietschrift fur Kardiologie*, Sep. 9, 1992 (German with English language summary).

Harrington, J.D., et al., The Palmaz-Schatz Stent, *Handbook of Cardiovascular Interventions/Vascular Internventions*, pp. 563-572 undated.

* cited by examiner

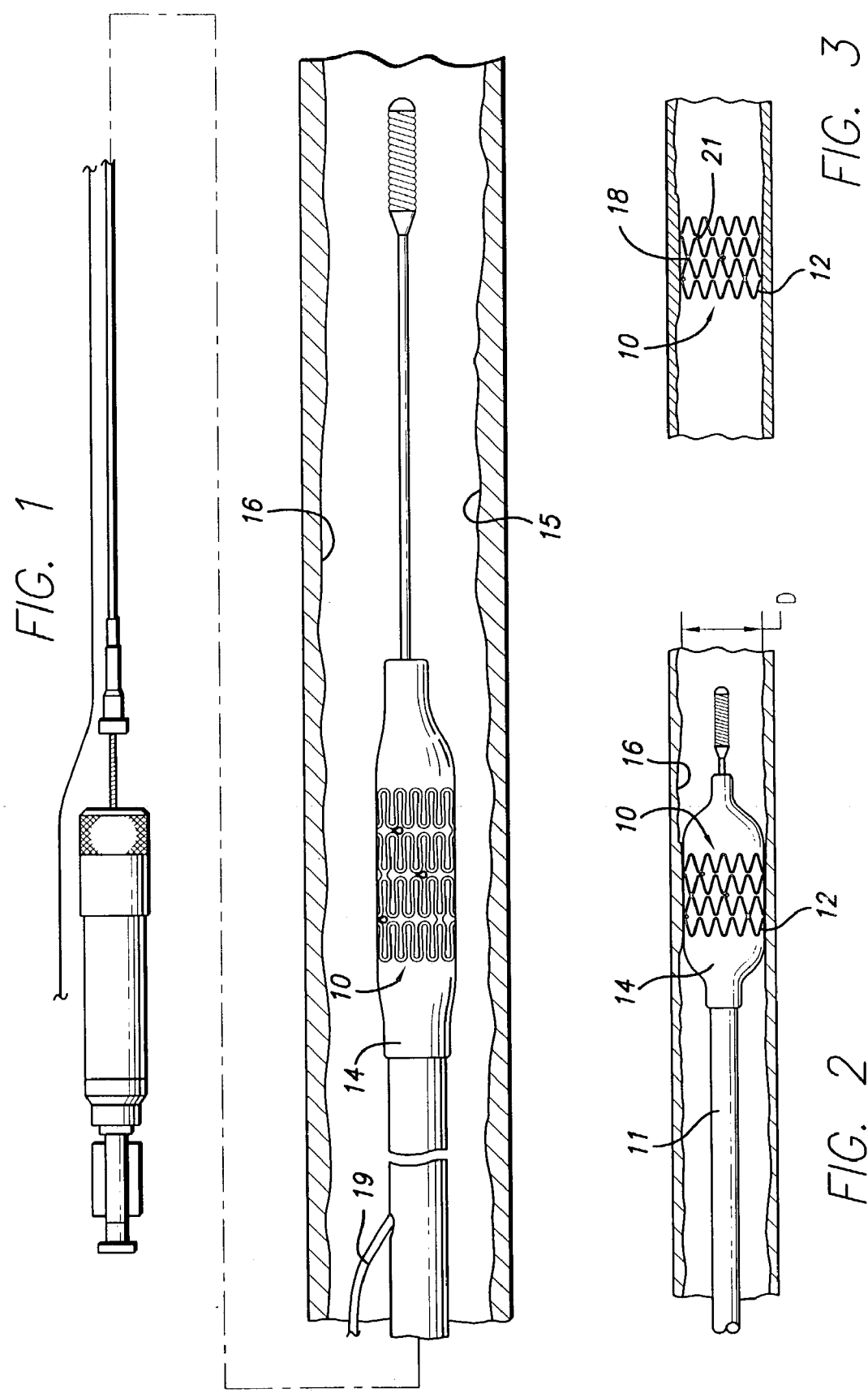

FLEXIBLE STENT

BACKGROUND OF THE INVENTION

This invention relates to expandable endoprosthesis devices, generally known as stents, which are designed for implantation in a patient's body lumen, such as arteries or blood vessels to maintain the patency thereof. These devices are particularly useful in the treatment and repair of blood vessels after a stenosis has been compressed by percutaneous transluminal coronary angioplasty (PTCA), or percutaneous transluminal angioplasty (PTA), or removed by atherectomy or other means.

Stents are generally cylindrically-shaped devices which function to hold open and sometimes expand a segment of a blood vessel or other lumen such as a coronary artery.

A variety of devices are known in the art for use as stents and have included balloon expandable stents having a variety of patterns; coiled wires in a variety of patterns that are expanded after being placed intraluminally on a balloon catheter; helically wound coiled springs manufactured from an expandable heat sensitive metal; and self expanding stents inserted in a compressed state and shaped in a zigzag pattern. One of the difficulties encountered using prior stents involved maintaining the radial rigidity needed to hold open a body lumen while at the same time maintaining the longitudinal flexibility of the stent to facilitate its delivery and accommodate the often tortuous path of the body lumen.

Another problem area has been the limiting range of expandability. Certain prior art stents expand only to a limited degree due to the uneven stresses created upon the stents during radial expansion. This necessitates providing stents with a variety of diameters, thus increasing the cost of manufacture. Additionally, having a stent with a wider range of expandability allows the physician to redilate the stent if the original vessel size was miscalculated.

Another problem with the prior art stents has been contraction of the stent along its longitudinal axis upon radial expansion of the stent. This can cause placement problems within the artery during expansion.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter.

What has been needed is a stent which has an enhanced degree of flexibility so that it can be readily advanced through tortuous passageways and radially expanded over a wider range of diameters with minimal longitudinal contraction. The expanded stent must also of course have adequate structural strength (hoop strength) to hold open the body lumen in which it is expanded. The present invention satisfies these needs.

SUMMARY OF THE INVENTION

The present invention is directed to stents having a high degree of flexibility along their longitudinal axis to facilitate delivery through tortuous body lumens, but which remain highly stable when expanded radially, to maintain the patency of a body lumen such as an artery or other vessel when implanted therein. The unique patterns and materials of the stents of the instant invention permit both greater longitudinal flexibility and enhanced radial expandability and stability compared to prior art stents.

Each of the different embodiments of stents of the present invention include a plurality of adjacent cylindrical rings which are generally expandable in the radial direction and arranged in alignment along a longitudinal stent axis. At least one link extends between adjacent cylindrical rings and connects them to one another. The rings and links may each be formed with a variety of undulations containing a plurality of alternating peaks and valleys. This configuration helps to ensure minimal longitudinal contraction during radial expansion of the stent in the body lumen. The undulations of the rings and links contain varying degrees of curvature in regions of the peaks and valleys and are adapted so that the radial expansion of the cylindrical rings are generally uniform around their circumferences during expansion of the stents from their contracted conditions to their expanded conditions.

The resulting stent structures are a series of radially expandable cylindrical rings which are spaced longitudinally close enough so that small dissections in the wall of a body lumen may be pressed back into position against the luminal wall, but not so close as to compromise the longitudinal flexibility of the stent both when being negotiated through the body lumens in their unexpanded state and when expanded into position. Upon expansion, each of the individual cylindrical rings may rotate slightly relative to their adjacent cylindrical rings without significant deformation, cumulatively providing stents which are flexible along their length and about their longitudinal axis, but which are still very stable in the radial direction in order to resist collapse after expansion.

The presently preferred structures for the expandable cylindrical rings which form the stents of the present invention generally have a plurality of circumferential undulations containing a plurality of alternating peaks and valleys where the rings are formed from a metallic material. The links interconnecting the rings may also have undulations and may be formed from a polymer or metal as well as being coated with a polymeric coating. In all embodiments, the series of links provide the stent with longitudinal and flexural flexibility while maintaining sufficient column strength to space the cylindrical rings along the longitudinal axis. The metallic material forming the rings provides the stent with the necessary radial stiffness after the stent is implanted into a body lumen.

In the case of a balloon expandable catheter system, the cylindrical rings and the links remain closely coupled from the time the stent is crimped onto the delivery system to the time the stent is expanded and implanted into a body lumen. Accordingly, the cylindrical rings have first delivery diameters in the crimped state of the stent and second larger implanted diameters in the expanded state of the stent.

The stent can generally be divided into three sections for illustration purposes. The sections include a proximal stent section, a center stent section and a distal stent section. The proximal stent section includes one proximal ring and a series of corresponding proximal links. The proximal links are attached to an adjacent center ring located in the center stent section. The center stent section includes a series of center rings along with a series of center links interconnecting the center rings. The distal stent section includes a distal ring and a series of distal links connected thereto. The distal links are also attached to an adjacent center ring in the center stent section.

The rings are each formed with circumferential undulations that may be described as a series of peaks, valleys and straight portions. For further clarification, each ring within the stent can be divided into three sections including a proximal ring section, a center ring section and a distal ring section. The proximal ring section includes the peaks while the distal ring section includes the valleys. In between the two sections the center ring section includes the straight portions.

The rings are aligned along the longitudinal axis and in the majority of embodiments arranged so that adjacent rings have peaks aligned with valleys. In this arrangement all adjacent rings are circumferentially offset from each other (out of phase) along the longitudinal axis of the stent so that they appear to be mirror images of each other. For example, the proximal ring forms the proximal end of the stent and includes valleys in its distal ring section. Adjacent the proximal ring is a center ring which is connected to the proximal rings with a series of proximal links as mentioned above. The proximal ring section of this center ring includes peaks which are aligned with the valleys of the proximal ring. Accordingly, the valleys of this center ring are aligned with the peaks of the adjacent center ring and so on for the length of the stent. In one embodiment mentioned below adjacent rings are out of phase to a lesser degree such that two rings separate completely out of phase rings.

The links interconnecting the adjacent rings may include straight portions and/or undulations. In all cases each link has a proximal link end and a distal link end. The proximal link end is attached to a distal section of one ring while the distal link end is attached to a proximal section of another adjacent ring.

In one embodiment, four links interconnect each pair of adjacent rings within the distal stent section and the proximal stent section while five links interconnect adjacent rings in the center stent section. Of these links, two (three in center section) are substantially straight and the remaining two links are more flexible with loop shapes and smaller cross-sectional areas. The two types of links are alternately arranged around the circumference of the stent so that the rigidity provided by the straight links is sufficiently offset by the flexibility provided by the loop-shaped links. The rings each include ten peaks and ten valleys and the loop-shaped rings between adjacent rings helps to prevent clamshell opening. Clamshell opening occurs when a stent is expanded and a portion of the stent between two adjacent rings separates abnormally. This abnormal operation may cause undesirable effects such as tissue prolapse, movement of the stent within a vessel and reduced coverage area.

In another embodiment three links interconnect each pair of adjacent rings rather than four and five links as discussed in the embodiment above. The rings also have nine peaks rather than ten as above. In this configuration, the links essentially couple every third undulation between adjacent rings. The links are all formed substantially straight rather than loop-shaped. The use of three links for every pair of adjacent rings provides uniform flexibility around the circumference of the stent.

In another embodiment adjacent rings are circumferentially offset with respect to each other along the longitudinal axis. The rings each have nine peaks and are offset such that two rings separate completely out of phase rings. Three links couple each pair of adjacent rings to reduce potential clamshell opening.

In another embodiment the rings each have ten peaks and adjacent rings are coupled by three links in the center stent section. The rings within the proximal stent section include undulations that, while being generally U-shaped, have curvatures incorporated therein to help retain the stent onto a delivery catheter. In the distal stent section and proximal stent section two rather than three links couple the rings to the center rings of the center stent section.

In all embodiments the rings and links may include reservoirs to retain therapeutic drugs. The reservoirs may be formed as either micro-channels or micro-depots within the rings or links. The material of the rings or links associated with these reservoirs may be either a polymer or a metal.

Each of the embodiments of the invention can be readily delivered to the desired luminal location by mounting them on an expandable member of a delivery catheter, for example a balloon, and passing the catheter-stent assembly through the body lumen to the implantation site. A variety of means for securing the stents to the expandable member on the catheter for delivery to the desired location are available. It is presently preferred to crimp the stent onto the unexpanded balloon. Other means to secure the stent to the balloon include providing ridges or collars on the inflatable member to restrain lateral movement, using bioabsorbable temporary adhesives, or a retractable sheath to cover the stent during delivery through a body lumen.

While the cylindrical rings and links incorporated into the stent are generally not separate structures when both are formed from a metallic material, they have been conveniently referred to as rings and links for ease of identification. Further, the cylindrical rings can be thought of as comprising a series of U-shaped structures in a repeating pattern. While the cylindrical rings are not divided up or segmented into U-shaped structures, the pattern of cylindrical rings resemble such configuration. The U-shaped structures promote flexibility in the stent primarily by flexing and may tip radially outwardly as the stent is delivered through a tortuous vessel.

The links which interconnect adjacent cylindrical rings can have cross-sections smaller, larger or similar to the cross-sections of the undulating components of the cylindrical rings. The links may be formed in a unitary structure with the expandable cylindrical rings, or they may be formed independently and mechanically secured between the expandable cylindrical rings. The links may be formed substantially linearly or with a plurality of undulations.

Preferably, the number, shape and location of the links can be varied in order to develop the desired coverage area and longitudinal flexibility. These properties are important to minimize alteration of the natural physiology of the body lumen into which the stent is implanted and to maintain the compliance of the body lumen which is internally supported by the stent. Generally, the greater the longitudinal flexibility of the stents, the easier and the more safely they can be delivered to the implantation site, especially where the implantation site is on a curved section of a body lumen, such as a coronary artery or a peripheral blood vessel, and especially saphenous veins and larger vessels.

The stent may be formed from a tube by laser cutting the pattern of cylindrical rings and links in the tube, by individually forming wire rings and laser welding them together, and by laser cutting a flat metal sheet in the pattern of the cylindrical rings and links and then rolling the pattern into the shape of the tubular stent and providing a longitudinal weld to form the stent.

Other features and advantages of the present invention will become more apparent from the following detailed description of the invention, when taken in conjunction with the accompanying exemplary drawings.

BRIEF DESCRIPTION OF THE DRAWINGS

FIG. 1 is an elevational view, partially in section, of a stent embodying features of the invention which is mounted on a delivery catheter and disposed within a damaged artery.

FIG. 2 is an elevational view, partially in section, similar to that shown in FIG. 1 wherein the stent is expanded within a damaged or diseased artery.

FIG. 3 is an elevational view, partially in section, depicting the expanded stent within the artery after withdrawal of the delivery catheter.

FIG. 8A is a cross-sectional view of a curved portion of the proximal rings shown in FIG. 8.

DETAILED DESCRIPTION OF THE PREFERRED EMBODIMENTS

Figure 4:
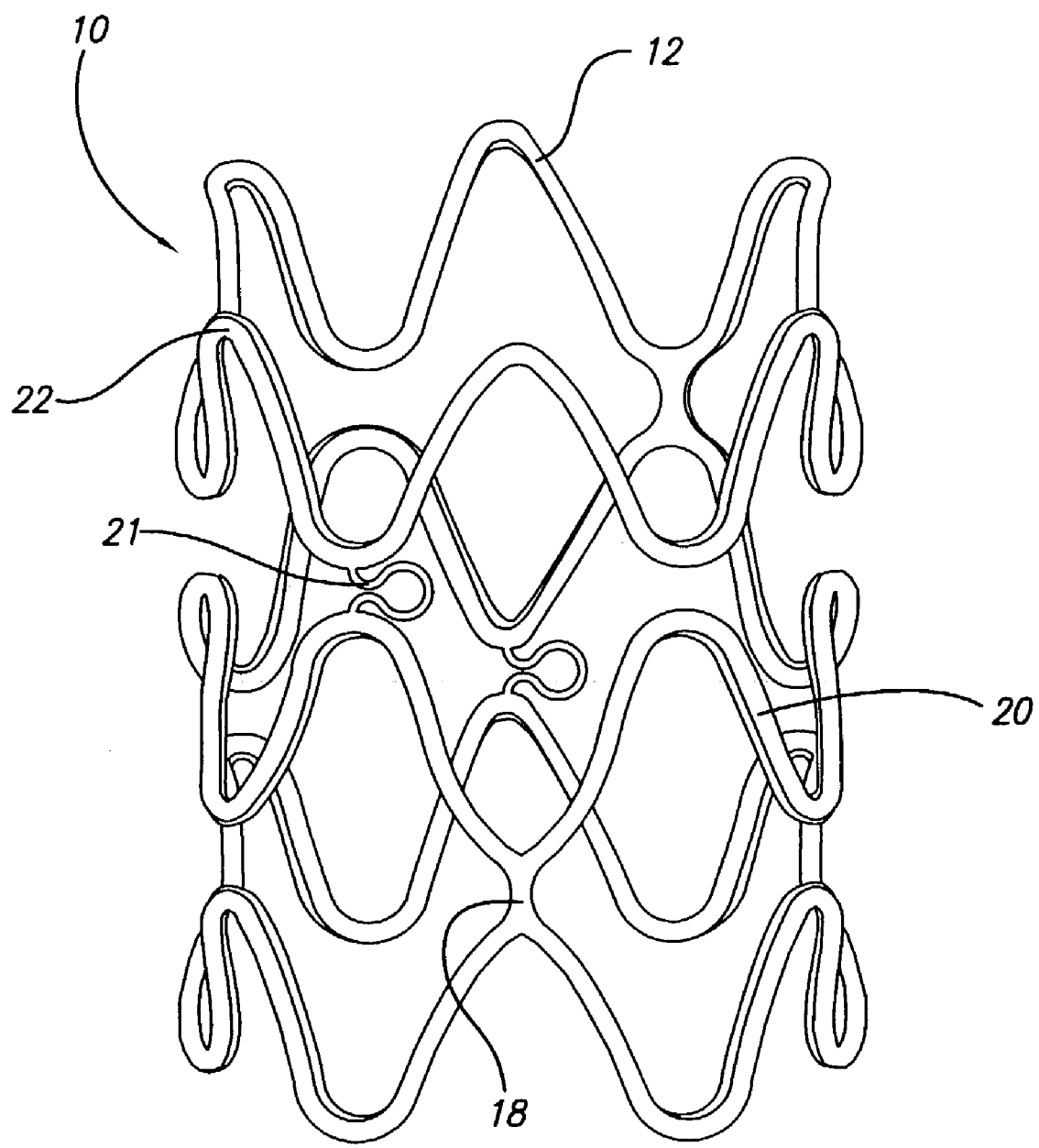
FIG. 4 is a perspective view of the stent of FIG. 3 in its expanded state depicting the undulating pattern along the peaks and valleys that form the cylindrical rings.

Before describing in detail an exemplary embodiment of a stent in accordance with the present invention, it is instructive to briefly describe a typical stent implantation procedure and the vascular conditions which are typically treated with stents. Referring now to FIG. 1, a stent 10 of the present invention is shown mounted on a catheter 11 having a lumen 19 and an inflation member (balloon) 14. The stent and catheter are shown inside the lumen of an arterial vessel 16. The stent is shown positioned across a small amount of arterial plaque 15 adhering to the lumen of the artery. In some procedures, a stent is directly implanted without a prior procedure, such as balloon angioplasties. In other procedures, the plaque is the remainder of an arterial lesion which has been previously dilated or radially compressed against the walls of the artery, or has been partially removed from the artery. Lesion dilation is typically accomplished by an angioplasty procedure, while lesion removal is typically accomplished by an atherectomy procedure. These and other procedures for the treatment of arterial lesions are well known to those skilled in the art.

With most lesion treatment procedures, the treated artery suffers a degree of trauma, and in a certain percentage of cases may abruptly collapse or may slowly narrow over a period of time due to neointimal hyperplasia which is referred to as restenosis. To prevent either of these conditions, the treated artery is often fitted with a prosthetic device, such as the stent 10 of the present invention. The stent provides radial support for the treated vessel and thereby prevents collapse of the vessel 16, and further provides scaffolding to prevent plaque prolapse within the lumen. The stent may also be used to repair an arterial dissection, or an intimal flap, both of which are sometimes found in the coronary arteries, peripheral arteries and other vessels. In order to perform its function, the stent must be accurately placed across the lesion site. Therefore, it is critical that the stent be sufficiently radiopaque so that the physician can visually locate the stent under fluoroscopy during the implantation procedure. However, it is equally important that the stent not be too radiopaque. If the stent is overly radiopaque, i.e., too bright, the physician's view of the lumen is compromised. This makes assessment of subsequent restenosis difficult. In cases where balloon markers are very close to the stent, the stent can blend in with the markers. Without precise visualization of the stent ends, accurate placement of the stent in a lesion, particularly in the case of an ostial lesion, can be compromised.

With continued reference to FIG. 1, in a typical stent placement procedure, a guiding catheter (not shown) is percutaneously introduced into the cardiovascular system of a patient through the femoral arteries by means of a conventional Seldinger technique, and advanced within a patient's vascular system until the distal end of the guiding catheter is positioned at a point proximal to the lesion site. A guide wire and the stent-delivery catheter 11 of the rapid exchange type are introduced through the guiding catheter with the guide wire sliding within the stent-delivery catheter. The guide wire is first advanced out of the guiding catheter into the arterial vessel 16 and is advanced across the arterial lesion. Prior to implanting the stent, the cardiologist may wish to perform an angioplasty or other procedure (e.g., atherectomy) in order to open and remodel the vessel and the diseased area.

Referring to FIG. 2, the stent delivery catheter assembly 11 is advanced over the guide wire so that the stent 10 is positioned in the target area. The stent-delivery catheter is subsequently advanced over the previously positioned guide wire until the stent is properly positioned across the lesion.

Referring now to FIGS. 2 and 3, once in position, the dilation balloon 14 is inflated to a predetermined size to radially expand the stent 10 against the inside of the artery wall and thereby implant the stent within the lumen of the artery 16. The balloon 14 is then deflated to a small profile so that the stent-delivery catheter may be withdrawn from the patient's vasculature and blood flow resumed through the artery.

The metallic cylindrical rings 12 of this embodiment are formed from tubular members and may be relatively flat in transverse cross-section. Thus, after implantation into the artery 16 as shown in FIG. 3, minimal interference with blood flow occurs. Eventually the stent becomes covered with endothelial cell growth, which further minimizes blood flow interference. As should be appreciated by those skilled in the art that, while the above-described procedure is typical, it is not the only method used in placing stents.

The stent patterns shown in FIGS. 1-3 are for illustration purposes only and can vary in size and shape to accommodate different vessels or body lumens. Further, the stent 10 is of a type that can be used in accordance with the present invention.

Links 18,21 interconnect adjacent cylindrical rings 12 and may have cross-sections smaller, larger or similar to the cross-sections of the undulating components of the expandable cylindrical rings. The number and location of the links connecting the rings together can be varied in order to vary the desired longitudinal and flexural flexibility in the stent assembly structure in the unexpanded as well as expanded condition of the stent. These properties are important to minimize alteration of the natural physiology of the body lumen into which the stent assembly is implanted and to maintain the compliance of the body lumen which is internally supported by the stent assembly. Generally, the greater the longitudinal and flexural flexibility of the stent assembly, the easier and the more safely it can be delivered to the target site.

With reference to FIG. 4, the stent 10 includes cylindrical rings 12 in the form of undulating portions. The undulating portions are made up of a plurality of U-shaped undulations 20 having radii that more evenly distribute expansion forces over the various members. After the cylindrical rings have been radially expanded, outwardly projecting edges 22 may be formed. That is, during radial expansion some of the U-shaped undulations may tip radially outwardly thereby forming outwardly projecting edges. These outwardly projecting edges can provide for a roughened outer wall surface of the stent and assist in implanting the stent in the vascular wall by embedding into the vascular wall. In other words, the outwardly projecting edges may embed into the vascular wall, for example arterial vessel 16, as depicted in FIG. 3. Depending upon the dimensions of the stent and the thickness of the various members making up the serpentine pattern, any of the U-shaped undulations may tip radially outwardly to form the projecting edges.

The cylindrical rings 12 can be nested such that adjacent rings slightly overlap in the longitudinal direction so that one ring is slightly nested within the next ring and so on. The degree of nesting can be dictated primarily by the length of each link, cylindrical ring, the number of undulations in the rings, the thickness of the rings, and the radius of curvature, of the rings all in conjunction with the crimped or delivery diameter of the stent. If the rings are substantially nested one within the other, it may be difficult to crimp the stent to an appropriate delivery diameter without the various struts overlapping. It is also contemplated that the rings may be slightly nested even after the stent is expanded, which enhances vessel wall coverage. In some circumstances, it may not be desirable to nest one ring within the other, which is also contemplated by the invention.

Figure 5:
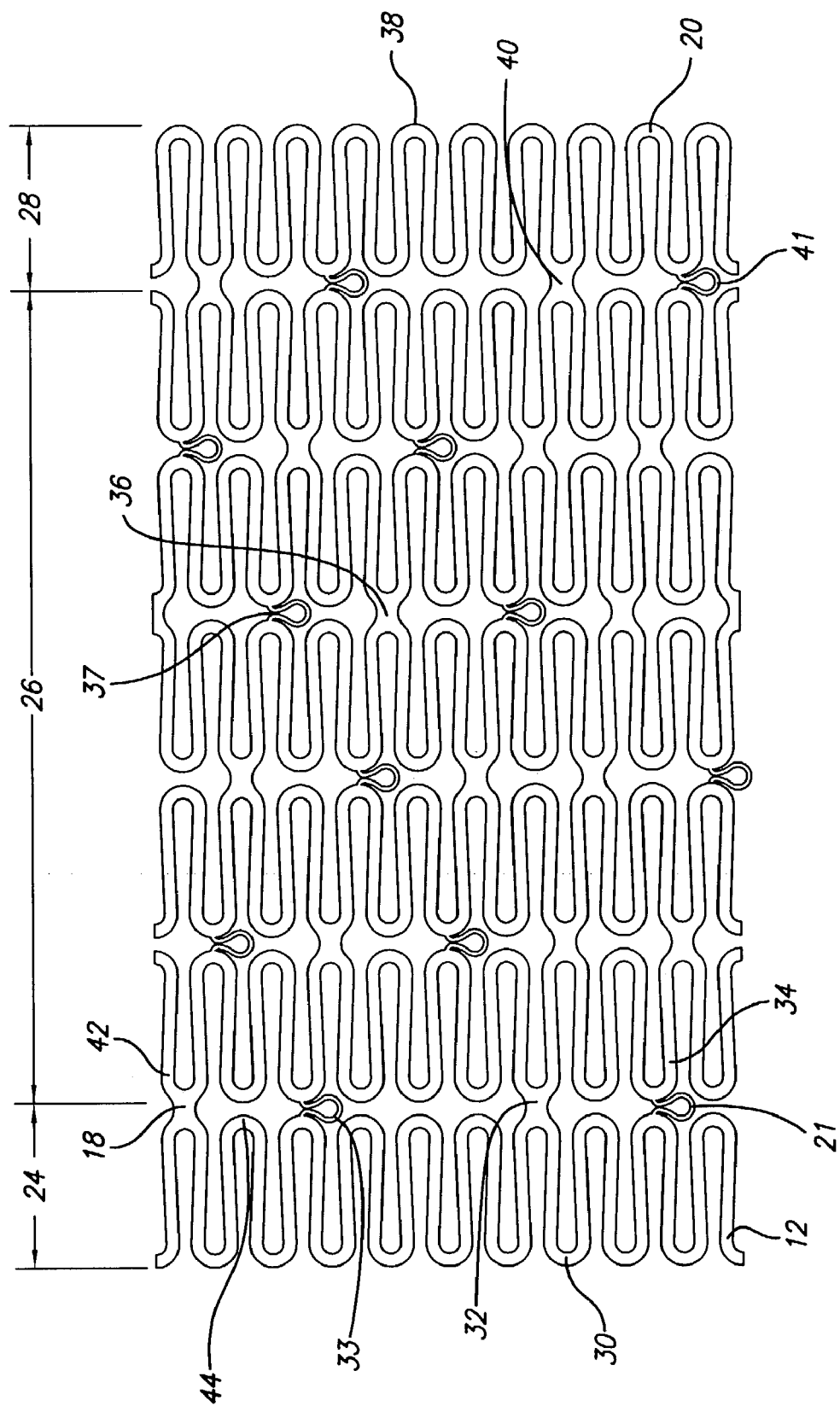
FIG. 5 is a plan view of a flattened section of the embodiment shown in FIGS. 1-4.

For the purpose of illustration only, the stent 10 is shown as a flat pattern in FIG. 5 so that the pattern of rings 12 and links 18,21 may be clearly viewed. Normally the stent of the present invention is formed of a cylindrical structure, however, it is beneficial to describe various parts to facilitate discussion. The rings in the present embodiment have an undulating shape including peaks 42 and valleys 44 formed as U-shaped undulations 20 which are out of phase with the U-shaped undulations of adjacent cylindrical rings. The particular pattern and how many undulations, or the amplitude of the undulations, are chosen to fill particular mechanical requirements for the stent, such as radial stiffness and longitudinal flexibility. Typically, each adjacent ring will be connected by at least one connecting link 18,21. The number of cylindrical rings incorporated into the stent can also vary according to design requirements taking into consideration factors such as radial stiffness and longitudinal flexibility.

The substantially straight links 18 also can be formed with an undulating pattern to enable the stent to have higher flexibility and deliverability and may be formed in a number of different patterns according to design requirements. For example, the links can be formed with more or less surface area, larger or smaller cross-sections, curves or oscillations, and a variety of other shapes according to design requirements.

The stent patterns shown in FIGS. 1-5 are for illustration purposes only and can vary in shape and size to accommodate different vessels or body lumens. Thus, rings 12 connected by links 18,21 can have any structural shapes and are not limited to the aforedescribed undulating rings including U-shaped portions. Links connecting the rings can also include oscillating patterns, sinusoidal patterns and zig-zag patterns. One aspect of the invention also provides for various anchoring mechanisms for attaching the links to the rings.

For illustration purposes an embodiment of the stent of the present invention shown in FIGS. 1-5 can generally be divided into a proximal stent section 24, a center stent section 26 and a distal stent section 28. The proximal stent section includes one proximal ring 30 and a series of corresponding proximal links 32,33. The proximal links are attached to a center ring 34 located in the center stent section. The center stent section includes other center rings and center links 36,37 interconnecting the center rings. The distal stent section includes a distal ring 38 and a series of distal links 40,41 connected thereto. Like the proximal links the distal links are attached to a center ring.

As shown in FIG. 5, adjacent rings 12 are arranged out of phase along the longitudinal axis of the stent so that adjacent rings have peaks 42 aligned with valleys 44. In this arrangement all adjacent rings appear to be mirror images of each other and out of phase. For example, the proximal ring 30 includes distal valleys and adjacent the proximal ring is a center ring 34 with proximal peaks. The peaks of the center ring are aligned with the valleys of the proximal ring so that these adjacent rings appear to be mirror images of each other. Accordingly, the valleys of this center ring are aligned with the peaks of the adjacent center ring and so on for the length of the stent.

In this embodiment the stent includes two types of links 18,21. The substantially straight links are important for maintaining the structural integrity of the stent and three of these links are used between adjacent center rings 34 to reduce potential clamshell opening. Clamshell opening may occur upon expansion of the stent when less than three links are used for every pair of adjacent rings. The loop-shaped links with relatively smaller cross-sectional areas also help to minimize the clamshell opening effect while minimally reducing the flexibility of the stent. In the proximal stent section 24 and distal stent section 28 two substantially straight links are utilized to maintain flexibility while two loop-shaped links are used between every pair of adjacent rings throughout the stent.

Figure 6:
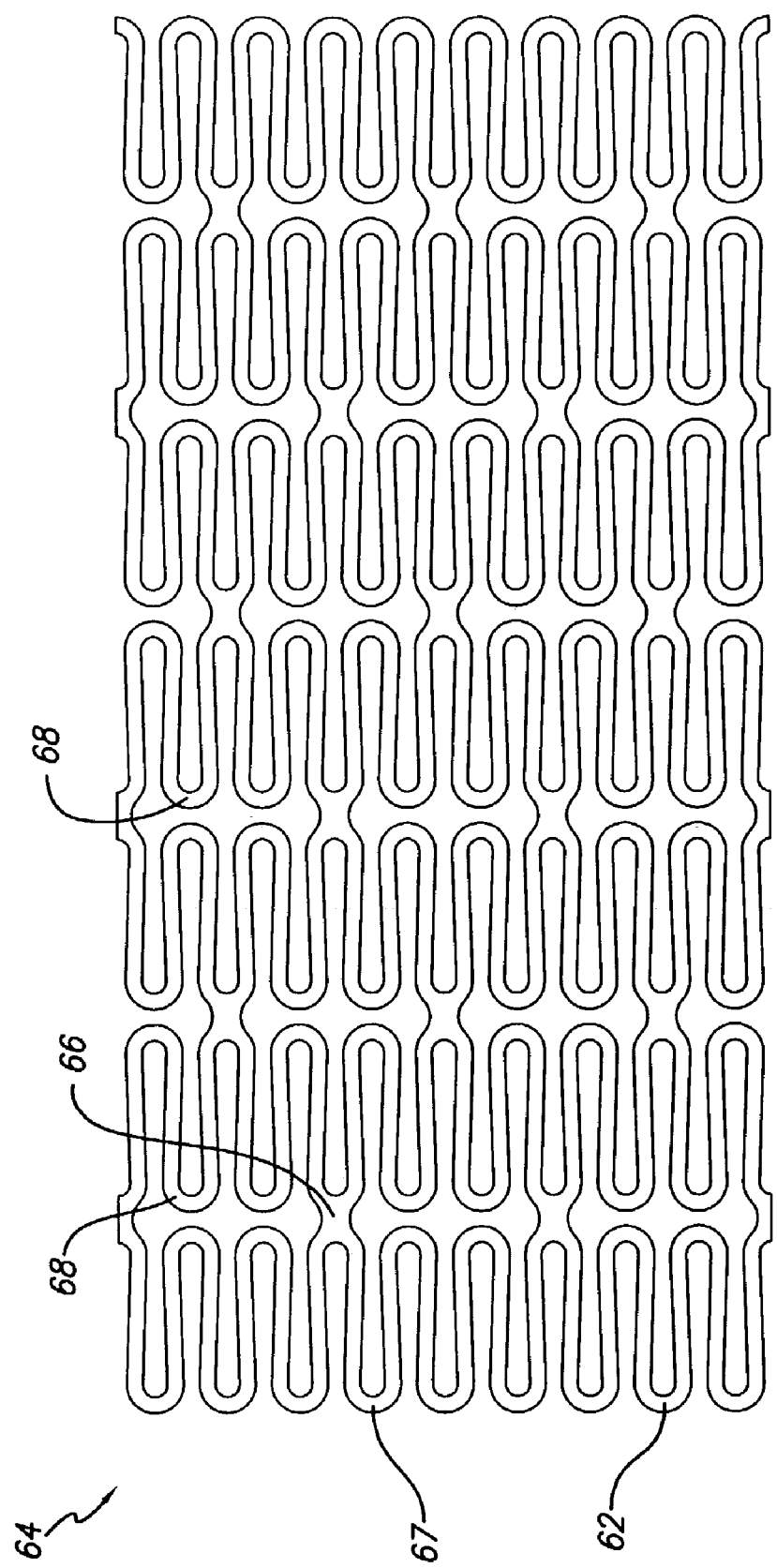
FIG. 6 is a plan view of a flattened section of one embodiment of a stent of the invention incorporating nine peaks within each ring.

In another embodiment shown in FIG. 6, a stent 64 includes links 66 which are all substantially straight and similarly sized. The rings 62 each incorporate undulations with nine peaks 68 rather than ten peaks 42 as in the embodiment shown in FIGS. 1-5. With a smaller number of undulations, there is more area between the peaks and valleys on each ring. The increased open area allows a delivery balloon to penetrate the stent farther when the stent is crimped onto a delivery catheter. This high degree of penetration helps to securely retain the stent. The links connect every third peak and valley of adjacent rings and are spaced evenly around the circumference of the stent to uniformly distribute load. The links also are circumferentially offset along the longitudinal axis of the stent so that flexibility is maximized.

Figure 7:
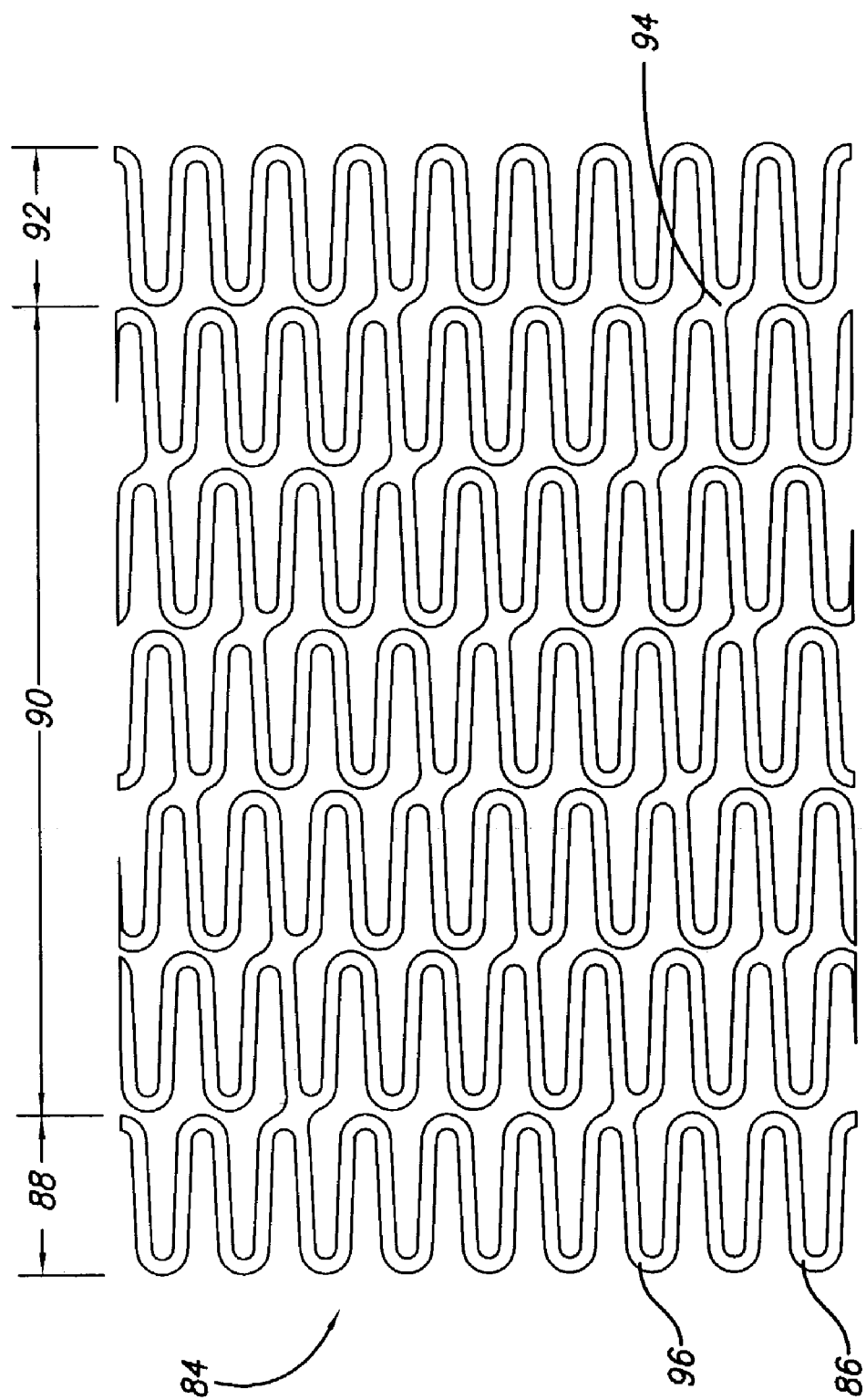
FIG. 7 is a plan view of a flattened section of one embodiment of a stent of the invention incorporating circumferentially offset rings.

In another embodiment shown in FIG. 7, a stent 84 includes undulating rings 86 that are circumferentially offset from each other along the longitudinal axis of the stent to a lesser degree than the rings in FIG. 6. The offset is such that two rings separate completely out of phase rings. In the proximal stent section 88 and the distal stent section 92 two links interconnect adjacent rings while in the center stent section 90 three links 94 interconnect adjacent rings. This configuration of links maximizes rigidity and minimizes the clamshell opening effect within the center stent section. The rings 86 each incorporate nine peaks 96 which help offset the rigidity provided by the three links for every pair of adjacent ring within the center section and the circumferential offset of the rings along the longitudinal axis. As in the embodiment shown in FIG. 6, the links are circumferentially offset along the longitudinal axis to enhance flexibility. The space between the nine peaks within the rings of the present embodiment also enables the stent to have improved retention on the delivery catheter similar to the embodiment shown in FIG. 7.

Figure 8:
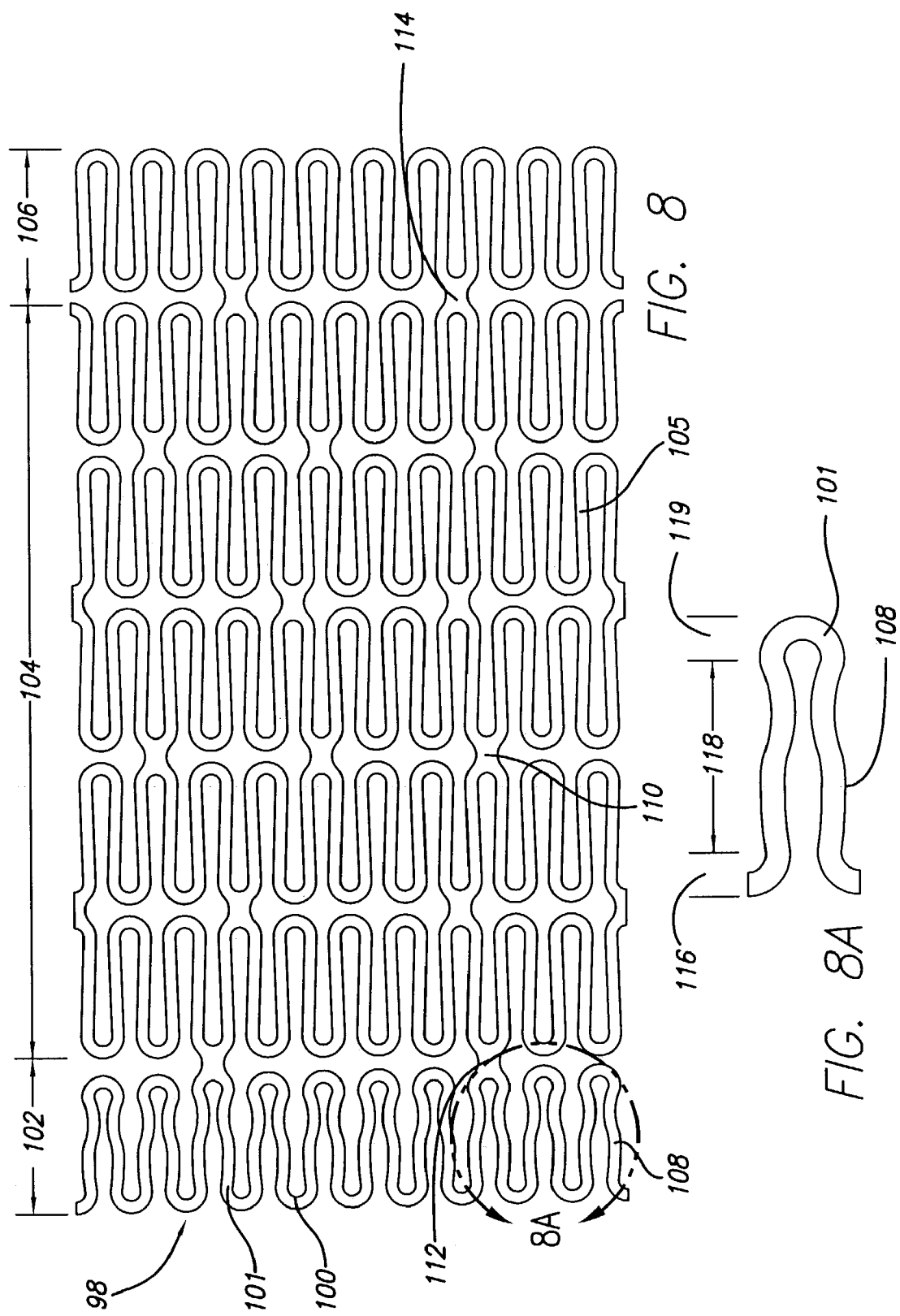
FIG. 8 is a plan view of a flattened section of one embodiment of a stent of the invention incorporating a modified U-shaped undulating ring within the proximal stent section.

In another embodiment shown in FIG. 8, a stent 98 includes modified U-shaped undulations 100 within the proximal ring 101 of the proximal stent section 102 while the center section 104 incorporates U-shaped undulations 105 as in FIGS. 1-7. The modified undulations include a series of curves 108 therein to help retain the stent onto the delivery catheter. More particularly, the curves allow the delivery balloon to be securely held within the rings and therefore help to prevent movement of the stent with respect to the balloon. As shown in detail in FIG. 8A, the proximal ring includes a proximal ring section 116, a center ring section 118 and a distal ring section 119. The curved portion of the modified U-shaped undulation is located in the center ring section while the proximal ring section and the distal ring section are substantially similar to those of the U-shaped undulations in the center stent section and distal stent section. Two links 112,114 are used to couple adjacent rings in the proximal stent section and the distal stent section while three links 110 are used in the center stent section to connect every adjacent ring. Due to the relatively small number of links coupling the proximal ring and the distal ring to the center rings, flexibility for this configuration is high within the distal stent section and proximal stent section while the center stent section retains a higher degree of rigidity.

Figure 9:
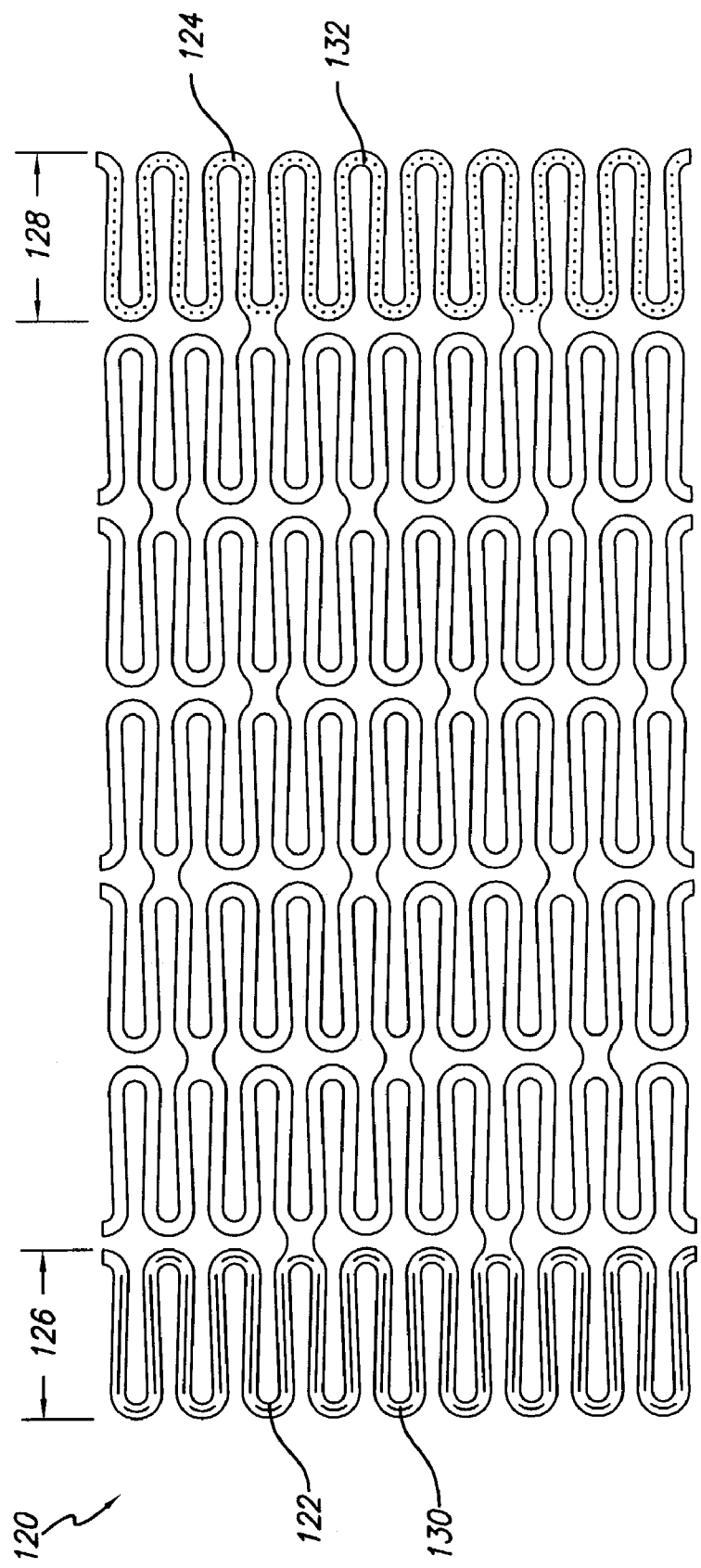
FIG. 9 is a plan view of a flattened section of one embodiment of a stent of the invention incorporating rings with micro-depots and micro-channels.

In another embodiment shown in FIG. 9, therapeutic drugs can be uniformly loaded and distributed through reservoirs in the proximal ring 122 and in the distal ring 124 to help prevent restenosis within the proximal stent section 126 and distal stent section 128 of a stent 120. More particularly, the proximal ring incorporates micro-channels 130 within its structure to help retain the therapeutic drug. Similarly, the distal ring incorporates micro-depots 132 which also help to retain the therapeutic drug. For illustration purposes both types of reservoirs are shown in the embodiment of FIG. 9 while in practice either or both may be incorporated into the stent. Additionally, either type of reservoir can be used on other rings within the stent and can be incorporated into the other embodiments as needed. For example, the micro-channels may be incorporated into the distal rings and the micro-depots may be incorporated into the proximal rings.

Figure 10:
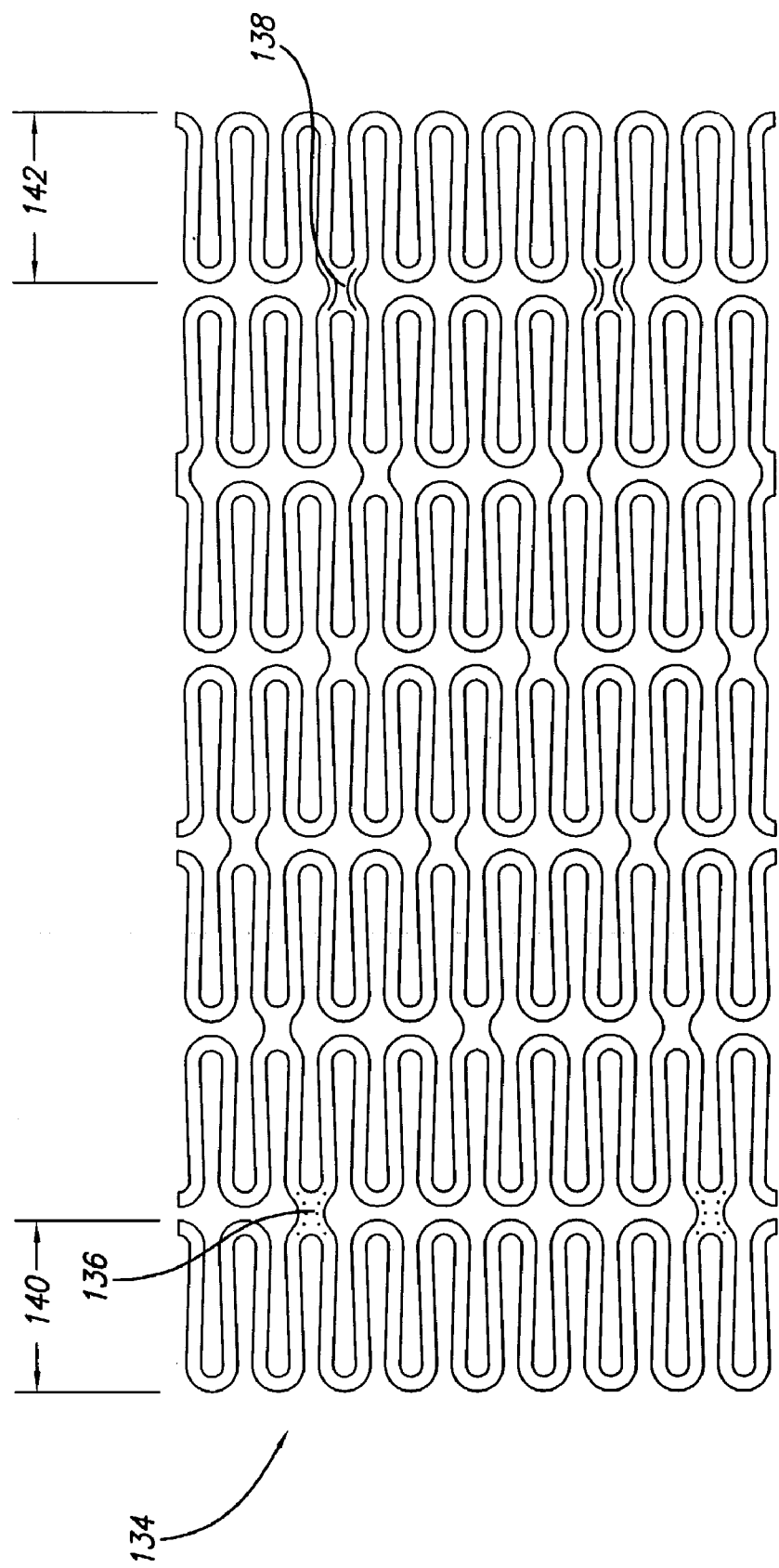
FIG. 10 is a plan view of a flattened section of one embodiment of a stent of the invention incorporating links with micro-depots and micro-channels.

In the embodiment shown in FIG. 10, a stent 134 includes reservoirs within the proximal links 136 and the distal links 138 similar to those in the proximal ring 122 and the distal ring 124 of the embodiment shown in FIG. 9. More particularly this embodiment includes two links within the proximal stent section 140 incorporating micro-depots and two distal links within the distal section 142 incorporating micro-channels, both of which help to uniformly retain and distribute a therapeutic drug. For illustration purposes both types of reservoirs are shown in the embodiment of FIG. 10 while in practice either or both may be incorporated into the stent. Additionally, either type of reservoir can be used on other links within the stent and can be incorporated into the other embodiments as needed. For example, the micro-channels may be incorporated into the proximal links and the micro-depots may be incorporated into the distal links.

In keeping with the invention, the links of any embodiment may be formed from a flexible polymeric material, that is bendable and flexible to enhance longitudinal and flexural flexibility of the stent. The polymeric material forming the links can be taken from the group of polymers consisting of polyurethanes, polyolefins, polyesters, polyamides, fluoropolymers and their co-polymers, polyetherurethanes, polyesterurethanes, silicone, thermoplastic elastomer (C-flex), polyether-amide thermoplastic elastomer (Pebax), fluoroelastomers, fluorosilicone elastomer, polydimethyl siloxones (PDMS), aromatic PDMS, silicon thermoplastic urethanes, poly (glycerol-sebacate)(PGS) (developed by Yadong Wang, MIT) and commonly referred to as biorubber, styrene-butadiene rubber, butadiene-styrene rubber, polyisoprene, neoprene (polychloroprene), ethylene-propylene elastomer, chlorosulfonated polyethylene elastomer, butyl rubber, polysulfide elastomer, polyacrylate elastomer, nitrile, rubber, a family of elastomers composed of styrene, ethylene, propylene, aliphatic polycarbonate polyurethane, polymers augmented with antioxidants, polymers augmented with image enhancing materials, polymers having a proton (H+) core, polymers augmented with protons (H+), butadiene and isoprene (Kraton), polyester thermoplastic elastomer (Hytrel), methacrylates, ethylene, acetate, alcohol, and polyvinyl alcohol.

The rings and the links (when metallic) may be made of suitable biocompatible material such as stainless steel, titanium, tungsten, tantalum, vanadium, cobalt chromium, gold, palladium, platinum, and iradium, and even high strength thermoplastic polymers. The stent diameters are very small, so the tubing from which they are made must necessarily also have a small diameter. For PTA applications, typically the stent has an outer diameter on the order of about 1.65 mm (0.065 inch) in the unexpanded condition, the same outer diameter of the tubing from which it is made, and can be expanded to an outer diameter of 5.08 mm (0.2 inch) or more. The wall thickness of the tubing is about 0.076 mm (0.003 inch). In the case of forming the stent from cobalt-chromium the wall thickness of the tubing may be reduced. For stents implanted in other body lumens, such as PTA applications, the dimensions of the tubing are correspondingly larger. While it is preferred that the stents be made from laser cut tubing, those skilled in the art will realize that the stent can be laser cut from a flat sheet and then rolled up in a cylindrical configuration with the longitudinal edges welded to form a cylindrical member.

The rings may also be made of materials such as superelastic (sometimes called pseudo-elastic) nickel-titanium (NiTi) alloys. In this case the rings would be formed full size but deformed (e.g. compressed) to a smaller diameter onto the balloon of the delivery catheter to facilitate intraluminal delivery to a desired intraluminal site. The stress induced by the deformation transforms the rings from an austenite phase to a martensite phase, and upon release of the force when the stent reaches the desired intraluminal location, allows the stent to expand due to the transformation back to the more stable austenite phase. Further details of how NiTi superelastic alloys operate can be found in U.S. Pat. Nos. 4,665,906 (Jervis) and 5,067,957 (Jervis). The NiTi alloy rings may be attached to the other rings through welding, bonding and other well known types of attachments.

The stent of the invention also can be coated with a drug or therapeutic agent. Further, it is well known that the stent (when both the rings and links are made from metal) may require a primer material coating such as a polymer to provide a substrate on which a drug or therapeutic agent is coated since some drugs and therapeutic agents do not readily adhere to a metallic surface. The drug or therapeutic agent can be combined with a coating or other medium used for controlled release rates of the drug or therapeutic agent. Representative examples of polymers that can be used to coat a stent in accordance with the present invention include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolicacid-co-trimethylene carbonate); polyphosphoester; polyphosphoester urethane; poly(amino acids); cyanoacrylates; poly(trimethylene carbonate); poly(iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; polybutylmethacrylate; rayon; rayon-triacetate; poly(glycerol-sebacate); cellulose acetate; cellulose butyrate; cellulose acetate butyrate; cellophane; cellulose nitrate; cellulose propionate; cellulose ethers; and carboxymethyl cellulose.

"Solvent" is a liquid substance or composition that is compatible with the polymer and is capable of dissolving the polymer at the concentration desired in the composition. Representative examples of solvents include chloroform, acetone, water (buffered saline), dimethylsulfoxide (DMSO), propylene glycol methyl ether (PM,) iso-propylalcohol (IPA), n-propylalcohol, methanol, ethanol, tetrahydrofuran (THF), dimethylformamide (DMF), dimethyl acetamide (DMAC), benzene, toluene, xylene, hexane, cyclohexane, heptane, octane, pentane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, formamide, hexafluoroisopropanol, 1,1,1-trifluoroethanol, and hexamethyl phosphoramide and a combination thereof. The therapeutic substance contained in the coating can be for inhibiting the activity of vascular smooth muscle cells. More specifically, the therapeutic substance can be aimed at inhibiting abnormal or inappropriate migration and/or proliferation of smooth muscle cells for the inhibition of restenosis. The therapeutic substance can also include any active agent capable of exerting a therapeutic or prophylactic effect in the practice of the present invention. For example, the therapeutic substance can be for enhancing wound healing in a vascular site or improving the structural and elastic properties of the vascular site. Examples of therapeutic agents or drugs that are suitable for use with the polymeric materials include sirolimus, everolimus, actinomycin D (ActD), taxol, paclitaxel, or derivatives and analogs thereof. Examples of agents include other antiproliferative substances as well as antineoplastic, antiinflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents that can be combined with the polymeric materials include antiplatelets, anticoagulants, antifibrins, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E-3B® (an antiplatelet drug from Centocor located in Malvern, Pa.). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as Captopril® (available from Squibb located in New York, N.Y.), Cilazapril® (available from Hoffman-LaRoche located in Basel, Switzerland), or Lisinopril® (available from Merck located in Whitehouse Station, N.J.); calcium channel blockers (such as Nifedipine), colchicine, fibroblast growth factor (FGF) antagonists, fish oil (omega 3-fatty acid), histamine antagonists, Lovastatin® (an inhibitor of HMG-CoA reductase, a cholesterol lowering drug from Merck), methotrexate, monoclonal antibodies (such as PDGF receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agents are known in the art. Furthermore, the calculation of dosages, dosage rates and appropriate duration of treatment are previously known in the art.

The stent of the present invention can be made in many ways. One method of making the stent is to cut a tubular member, such as stainless steel tubing to remove portions of the tubing in the desired pattern for the stent, leaving relatively untouched the portions of the metallic tubing which are to form the stent. In accordance with the invention, it is preferred to cut the tubing in the desired pattern by means of a machine-controlled laser as is well known in the art.

After laser cutting the stent pattern the stents are preferably electrochemically polished in an acidic aqueous solution such as a solution of ELECTRO-GLO#300, sold by ELECTRO-GLO Co., Inc. in Chicago, Ill., which is a mixture of sulfuric acid, carboxylic acids, phosphates, corrosion inhibitors and a biodegradable surface active agent. Other electropolishing solutions are well known in the art. The stents may be further treated if desired, for example by applying a biocompatible coating.

Other methods of forming the stent of the present invention can be used, such as chemical etching; electric discharge machining; laser cutting a flat sheet and rolling it into a cylinder; and the like, all of which are well known in the art at this time.

The stent of the present invention also can be made from metal alloys other than stainless steel, such as shape memory alloys. Shape memory alloys are well known and include, but are not limited to, nickel-titanium and nickel/titanium/vanadium. Any of the shape memory alloys can be formed into a tube and laser cut in order to form the pattern of the stent of the present invention. As is well known, the shape memory alloys of the stent of the present invention can include the type known as thermoelastic martensitic transformation, or display stress-induced martensite. These types of alloys are well known in the art and need not be further described here.

Importantly, a stent formed of shape memory alloys, whether the thermoelastic or the stress-induced martensite-type, can be delivered using a balloon catheter of the type described herein, or in the case of stress induced martensite, be delivered via a catheter without a balloon or a sheath catheter.

While the invention has been illustrated and described herein, in terms of its use as an intravascular stent, it will be apparent to those skilled in the art that the stent can be used in other body lumens. Further, particular sizes and dimensions, number of peaks per ring, materials used, and the like have been described herein and are provided as examples only. Other modifications and improvements may be made without departing from the scope of the invention.

What is claimed is:

1. An intravascular stent while in an unexpanded state, comprising:
   a distal section, a proximal section, and a center section there between;
   the distal section and the proximal section each having a single cylindrical ring and the center section having a plurality of cylindrical rings;
   the cylindrical ring of the distal section and the cylindrical rings of the center section having U-shaped undulations with peaks and valleys, wherein each peak is connected to a valley by a first segment that extends along most of the distance between such peak and valley; and
   the cylindrical ring in the proximal section having U-shaped undulations with peaks and valleys, wherein each peak is connected to a valley by a second segment that extends along most of the distance between such peak and valley;
   wherein said first segments have a shape that is different than the shape of said second segments as each of said first segments defines a substantially straight line while each of said second segments defines a series of curves.

2. The stent of claim 1, wherein adjacent cylindrical rings are connected by links.

3. The stent of claim 2, wherein two links connect the cylindrical ring in the distal section to an adjacent cylindrical ring in the center section.

4. The stent of claim 2, wherein two links connect the cylindrical ring in the proximal section to an adjacent cylindrical ring in the center section.

5. The stent of claim 2, wherein three links connect adjacent cylindrical rings in the center section.

6. The stent of claim 2, wherein the cylindrical rings and the links are formed from a metallic material taken from the group of metals consisting of stainless steel, titanium, tungsten, tantalum, vanadium, nickel-titanium, cobalt-chromium, gold, palladium, platinum and platinum-iridium.

7. The stent of claim 2, wherein at least a portion of the stent is coated with a therapeutic drug.

8. The stent of claim 7, wherein at least one of the links includes micro depots for receiving the therapeutic drug.

9. The stent of claim 7, wherein at least one of the links includes micro channels for receiving the therapeutic drug.

10. The stent of claim 7, wherein at least one ring other than a center ring includes micro depots for receiving the therapeutic drug.

11. The stent of claim 7, wherein at least one ring other than a center ring includes micro channels for receiving the therapeutic drug.

* * * * *